(12) United States Patent
Schouwink et al.

(10) Patent No.: US 11,317,788 B2
(45) Date of Patent: May 3, 2022

(54) OPTICAL SYSTEM OF A STEREO VIDEO ENDOSCOPE WITH A LATERAL VIEWING DIRECTION, AND METHOD TO PRODUCE THE SAME

(71) Applicant: OLYMPUS WINTER & IBE GMBH, Hamburg (DE)

(72) Inventors: Peter Schouwink, Hamburg (DE); Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 766 days.

(21) Appl. No.: 16/260,501

(22) Filed: Jan. 29, 2019

(65) Prior Publication Data

US 2019/0167082 A1    Jun. 6, 2019

Related U.S. Application Data

(63) Continuation of application No. PCT/EP2017/068779, filed on Jul. 25, 2017.

(30) Foreign Application Priority Data

Aug. 2, 2016   (DE) .................... 10 2016 214 272.0

(51) Int. Cl.
*A61B 1/00*       (2006.01)
*A61B 1/04*       (2006.01)
(Continued)

(52) U.S. Cl.
CPC ........ *A61B 1/00193* (2013.01); *A61B 1/0011* (2013.01); *A61B 1/00096* (2013.01);
(Continued)

(58) Field of Classification Search
CPC .......... H04N 13/239; H04N 2005/2255; A61B 1/0093; A61B 1/041; A61B 1/05
(Continued)

(56) References Cited

U.S. PATENT DOCUMENTS 5,689,365 A    11/1997  Takahashi
5,861,987 A     1/1999  Nakamura et al.
(Continued)

FOREIGN PATENT DOCUMENTS

CN    102985867 A    3/2013
CN    104049366 A    9/2014
(Continued)

OTHER PUBLICATIONS

Chinese Office Action dated Oct. 23, 2020 in Chinese Patent Application No. 201780047778.X.
International Search Report dated Oct. 30, 2017 received in PCT/EP2017/068779.

*Primary Examiner* — William C. Dowling
(74) *Attorney, Agent, or Firm* — Scully, Scott, Murphy & Presser, P.C.

(57) ABSTRACT

An optical system for use with a stereo video endoscope with a fixed, lateral viewing direction, including: laterally-viewing distal and proximal optical assemblies, similarly configured left and right lens system channels; the distal optical assembly couples incident light from an object space into the left and right lens system channels; the distal optical assembly includes an entrance lens, a deflection prism group and an exit lens in a direction of incident light; the deflection prism group includes first and second prisms in the direction of incident light; the first prism includes first entrance and first exit sides at an angle relative thereto; the second prism includes a second entrance side, a reflection side and a second exit side; and the first entrance side of the first prism and the reflection side of the second prism enclose an angle that is greater than a total reflection angle of the second prism.

13 Claims, 3 Drawing Sheets

(51) Int. Cl.
  *G02B 23/24*   (2006.01)
  *H04N 13/239*  (2018.01)
  *A61B 1/05*    (2006.01)
  *H04N 5/225*   (2006.01)

(52) U.S. Cl.
  CPC ............... *A61B 1/042* (2013.01); *A61B 1/05* (2013.01); *G02B 23/2415* (2013.01); *G02B 23/2423* (2013.01); *G02B 23/2484* (2013.01); *H04N 5/2254* (2013.01); *H04N 13/239* (2018.05); *H04N 2005/2255* (2013.01)

(58) Field of Classification Search
  USPC .......................................................... 353/81
  See application file for complete search history.

(56) References Cited

U.S. PATENT DOCUMENTS

| | | | |
|---|---|---|---|
| 10,441,138 B2 * | 10/2019 | Zhao | A61B 1/042 |
| 11,224,333 B2 * | 1/2022 | Zhao | G02B 23/243 |
| 2014/0135577 A1 | 5/2014 | Baumann et al. | |
| 2016/0154231 A1 | 6/2016 | Zhao et al. | |
| 2019/0216302 A1 * | 7/2019 | Schouwink | A61B 1/00193 |
| 2019/0285869 A1 * | 9/2019 | Zhao | G02B 27/0018 |
| 2020/0355909 A1 * | 11/2020 | Zhao | A61B 1/00096 |
| 2020/0363624 A1 * | 11/2020 | Zhao | G02B 23/2423 |

FOREIGN PATENT DOCUMENTS

| | | |
|---|---|---|
| DE | 10 2013 215 422 A1 | 2/2015 |
| DE | 10 2014 206 513 A1 | 10/2015 |
| EP | 2 730 210 A1 | 10/2013 |

* cited by examiner

OPTICAL SYSTEM OF A STEREO VIDEO ENDOSCOPE WITH A LATERAL VIEWING DIRECTION, AND METHOD TO PRODUCE THE SAME

CROSS-REFERENCE TO RELATED APPLICATION

The present application is a continuation of PCT/EP2017/068779 filed on Jul. 25, 2017, which is based upon and claims the benefit to DE 10 2016 214 272.0 filed on Aug. 2, 2016, the entire contents of each of which are incorporated herein by reference.

BACKGROUND

Field

The present disclosure relates to an optical system of a stereo video endoscope with a lateral viewing direction, and in particular, an optical system of a stereo video endoscope with a lateral viewing direction comprising a laterally-viewing distal optical assembly and a proximal optical assembly, wherein the proximal optical assembly comprises a left lens system channel and a right lens system channel that are designed similarly, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side.

Moreover, the present disclosure relates to a stereo video endoscope with a lateral viewing direction and a method to produce an optical system of a stereo video endoscope with a lateral viewing direction, wherein the stereo video endoscope comprises a laterally-viewing distal optical assembly and a proximal optical assembly, and wherein the proximal optical assembly comprises a left lens system channel and a right lens system channel that are designed similarly, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side.

Prior Art

Video endoscopes in which the light entering at a distal tip of an endoscope shaft is directed through an optical system onto one or more images sensors, are known in different designs. There are endoscopes with a direct view, a so-called 0° viewing direction, endoscopes with a (fixed) lateral viewing direction as well as endoscopes with an adjustable viewing direction (also called V-DOV endoscopes).

Moreover, stereo video endoscopes are known, which are designed to record a stereoscopic image pair and/or two stereoscopic video channels. With such instruments, it is possible to create a 3D image of an object in an examination or operating room lying distally in front of the end of the endoscope shaft.

Stereo video endoscopes with a lateral viewing direction are laterally-viewing endoscopes with a fixed viewing direction that deviates from the direct view. Such endoscopes frequently comprise a prism arrangement consisting of a plurality of prisms that reflect the light beams twice which enter the optical system from the object space at an angle to the longitudinal axis of the endoscope shaft and on the correct side in the direction of the endoscope shaft. Such an endoscope is for example known from DE 10 2014 206 513 A1 by Olympus Winter & Ibe, Hamburg.

A deflection prism arrangement of such a stereo video endoscope typically comprises two or three prisms. The prisms are repeatedly cemented to each other at their common boundary surfaces. In such a deflection prism arrangement, the reflection of the incident beams of light occurs at two reflecting boundary surfaces of a second prism that are angled relative both to the optical axis of the entrance lens as well as to the longitudinal axis of the endoscope shaft. The second prism of the deflection prism arrangement is located, in the direction of incident light, behind a first prism that is arranged directly behind the entrance lens. The angled reflecting boundary surface of the second prism at which the second reflection occurs partially forms a common boundary surface with the first prism through which the incident light beams first pass.

The entrance lens of the optical system of such a stereo video endoscope defines the optical axis of the optical system. The optical system comprises apertures or menisci that establish a field of view, or respectively the opening angle of the optical system. Beams of light that enter the optical system within the field of view are imaged by the optical system on one or more image sensors. Beams of light that enter the optical system from outside of the field of view frequently cause reflections within the optical system and generate so-called "ghost images" or "flares".

A known deflection prism group in which such ghost images can arise comprises a first prism and a second prism that are cemented to each other. The first prism has an entrance side and an exit side, wherein the entrance side is angled relative to the exit side. The exit side of the first prism directly borders the second entrance side of the second prism. For example, the first and the second prism are cemented to each other at these two sides. The second prism furthermore comprises a reflection side and a second exit side. Light that enters the deflection prism group outside of the field of view passes through the entrance side of the first prism and exits its exit side. The light then passes directly through the second entrance side into the second prism, is reflected on the reflection side within the second prism and leaves it at the exit side.

A peripheral light beam entering the optical system at a large angle relative to the optical axis of the entrance lens passes through the entrance lens into the first prism and passes through its entrance side and exit side. The light beam also passes through the second entrance side of the second prism at the same time as the first exit side. As already mentioned, these two prism surfaces can be cemented to each other. The light beam is then reflected on the reflection side of the second prism and contacts the common boundary surface between the first and second prism at a sharp angle, i.e., contacts the second entrance side of the second prism from the rear side. There, the light beam undergoes Fresnel reflection or total reflection and is reflected back to the reflection side of the second prism. From there, it again passes to the second entrance side of the second prism and is again reflected e.g. with total reflection by this boundary surface from the inside. Then the light beam passes into a left or right lens system channel where it generates a ghost image. This quadruple reflection in the deflection prism group which is known per se is undesirable.

FIG. 1 shows an optical system 20 as used in stereo video endoscopes 2 according to the prior art.

The optical system 20 defines the fixed, lateral viewing direction of the stereo video endoscope 2. The optical axis 22 encloses a fixed angle of for example 30° with the direction of longitudinal extension L of the endoscope shaft 6. The optical system 20 comprises a laterally-viewing distal optical assembly 24 and a proximal optical assembly 26. Light entering through the entrance window 10 from the object space 11 first contacts the entrance lens 28 and then enters a deflection prism group 30 of the distal optical assembly 24. The deflection prism group 30 sequentially comprises a first prism 32 and a second prism 34 in the direction of incident light.

In the direction of incident light, the beams of light that leave the entrance lens 28 first pass through a first entrance side 36 of the first prism 32. The beams of light pass through the body of the first prism 32 and reach its first exit side 38. The first exit side 38 is at an angle relative to the first entrance side 36. The first prism 32 and the second prism 34 are for example cemented to each other. The second prism 34 comprises a second entrance side 40 through which the light exiting the first prism 32 through its first exit side 38 enters the second prism 34. The first exit side 38 of the first prism 32 and the second entrance side 40 of the second prism 34 are cemented to each other in the portrayed example. The second prism 34 furthermore comprises a reflection side 42 that is at an angle relative to the second entrance side 40. The beams of light entering the second prism 34 through the second entrance side 40 are reflected on the reflection side 42 of the second prism 34. From there, they contact the second entrance side 40 of the second prism 34 from the rear side. The entrance side 40 is for example coated with a reflective coating in the top region where it does not border the exit side 38 of the first prism 32. Furthermore, alternatively to cementing the first and second prism 32, 34, a mask is arranged between the exit side 38 of the first prism 32 and entrance side 40 of the second prism 34. This mask causes an air gap between the exit side 38 and the entrance side 40 so that the light beams reflected from the inside on the entrance side 40 are totally reflected on the glass/air boundary surface. The beams of light are reflected on the rear side of the entrance side 40 at an angle such that they then leave the second prism 34 at its second exit side 44. From there, the beams of light continue in the direction of incident light to reach an exit lens 46 of the distal optical assembly 24.

The proximal optical assembly 26 comprises a left lens system channel 48L and a right lens system channel 48R. The left and the right lens system channels 48L, 48R are constructed in the same way or identically. They are furthermore arranged such that a left optical axis (not shown in FIG. 1) and a right optical axis (also not shown) of the left, or respectively right lens system channel 48L, 48R are aligned parallel to each other. The left lens system channel 48L comprises an imaging left lens group 50L that images the incident light on a left image sensor 52L. Correspondingly, the right lens system channel 48R comprises an imaging right lens group 50R that images the incident light on a right image sensor 52R.

The distal optical assembly 24 is configured to couple incident beams of light from the object space 11 both into the left lens system channel 48L as well as into the right lens system channel 48R.

With endoscopes as they are known from the prior art, the reflection side 42 of the second prism 34 is entirely provided with a reflective coating. For example, aluminum (Al) or silver (Ag) is vapor-deposited onto the outside of the second prism 34 on the reflection side 42.

The surface of the reflection side 42 of the second prism 34 is substantially larger with stereo video endoscopes than with endoscopes that do not provide stereoscopic images. This is necessary in order to enable a very large spacing of the left and right stereo channel. Such a large stereo base enables a strong 3-D effect.

Such a prism construction is however associated with the technical disadvantage that multiple reflections quickly arise which generate a so-called ghost image. Such ghost images are generated by peripheral light beams that enter the optical system 20 from the object space 11 at a wide angle relative to the optical axis 22.

Such a peripheral light beam passes through the entrance lens 28 into the first prism 32 and from there into the second prism 34. It contacts the reflection side 42 of the second prism 34, is reflected there, and contacts the boundary surface at a sharp angle between the first and the second prism 32, 34. From there, it is reflected back to the reflection side 42 of the second prism 34 and again reaches the second entrance side 38 of the second prism 34. Total reflection again occurs at this boundary surface so that the light beam then leaves the deflection prism assembly 30 through the exit side 44 and generates a ghost image in the left or right lens system channel 48L, 48R.

SUMMARY

It is therefore an object to present an optical system of a stereo video endoscope with a fixed, lateral viewing direction, a stereo video endoscope with a fixed, lateral viewing direction, as well as a method for producing and repairing an optical system of a stereo video endoscope with a fixed, lateral viewing direction that is less sensitive to incident beams of light from outside of the field of view, such as, ghost images.

Such object can be achieved by an optical system of a stereo video endoscope with a fixed, lateral viewing direction comprising a laterally-viewing distal optical assembly and a proximal optical assembly, wherein the proximal optical assembly comprises a left lens system channel and a right lens system channel that are similarly configured, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side wherein the optical system can be further developed in that the first entrance side and the reflection side enclose an angle that is greater than a total reflection angle of the second prism.

Beams of light entering the optical system that enter the optical system from a field of view in the object space pass through the first entrance side of the first prism, are reflected at the boundary surface of the prism body and pass through the first exit side of the first prism. The first exit side of the first prism can be cemented to the second entrance side of the second prism. The beams of light pass through this boundary surface to the second entrance side of the second prism. They are deflected at the boundary surface of the prism body and pass to the rear reflection side of the second prism. From there, the beams of light are reflected back to the second entrance side of the second prism and undergo total reflection in the prism body within the prism body of the second prism at this boundary surface. The beams of light are hence reflected at an inner side of the second entrance side. From there, the beams of light leave the deflection prism group through the exit side of the second prism.

In the context of the present description, "total reflection angle" is understood to be the critical angle of total reflection. This angle is determined by the material of the first and second prism, or more precisely, by the refraction index of the materials used. The first prism and the second prism can be made of identical material, for example from the same type of glass.

The total reflection angle $\Theta_C$ is for example calculated using formula (1):

$$\Theta_C = \arcsin(n1/n2), \tag{1}$$

where n1=1 stands for air, and n2>1 is the refraction index of the prism material.

This is the refraction index that is used in Snell's law of refraction. The complex refraction index that is indicated as a complex number to take into account the absorption of the wave in the medium is thus not used.

It is furthermore provided that the left lens system channel can have a left optical axis, and the right lens system channel can have a right optical axis. The left optical axis and the right optical axis can be aligned parallel to each other.

In the context of the present disclosure, a "lateral viewing direction" or the term "laterally viewing" is understood as follows: The stereo video endoscope has a shaft. This shaft is rigid or flexible. In the case of a rigid shaft, it has a direction of longitudinal extension. In the case of a flexible shaft, the shaft extends in a direction of longitudinal extension at a distal end region. The viewing direction of the endoscope forms an angle with its direction of longitudinal extension that is different from zero. This angle is constant. For example, such an angle is 30°.

In the provided optical systems, a quadruple reflection from the boundary surfaces of the deflection prism group as is known per se from the prior art is advantageously excluded. With stereo video endoscopes, the reflective surface of the second prism must be greater than is the case with prisms of endoscopes that do not provide a stereoscopic image. This is necessary since the greatest possible stereo base should be realized for the right and left stereo channel. A large stereo base makes it possible to create a large 3-D effect. This design requirement leads to the aforementioned danger of multiple reflections, such as the described quadruple reflection. These reflections create undesirable ghost images. By the arrangement of the first entrance side and the reflection side at the described angle, such (multiple) reflections are effectively suppressed.

According to an embodiment, the optical system can be configured such that incident light beams from a field of view of the optical system contact the reflection side of the second prism at an angle that is greater than the total reflection angle.

In this context, the optical system can comprise at least one aperture that borders the field of view of the optical system, wherein the angle between the first entrance side and the reflection side is adjusted taking into account a material of the second prism that establishes a refraction index and hence a total reflection angle, and taking into account a maximum viewing angle that is established by the field of view such that total reflection of all incident light beams from the field of view occurs at the reflection side of the second prism.

Due to this optimization of the relationships between the angle of incidence controlled by apertures or menisci at the first entrance side of the first prism, all of the beams of light entering the optical system from the interior of the field of view are totally reflected on the reflection side of the second prism.

Such an optical system furthermore can provide that the reflection side of the second prism is optionally uncoated, or is provided with an anti-reflective coating. Furthermore, the reflection side can be completely or extensively uncoated or completely or extensively provided with an anti-reflective coating.

A coating can be provided as the anti-reflective coating as is used in tempering photographic optical systems. In that context, anti-reflective coatings are used to reduce the degree of reflection of the optical surfaces of lenses, objective lenses, prisms or plates and increase transmission. Frequently tempering is spoken of in the case of objective lenses and eyepieces, and frequently anti-reflection treatment is spoken of in the case of glasses or inspection windows.

According to another embodiment, the optical system can be configured such that a first partial surface of the reflection side of the second prism is provided with a reflective coating, and a second partial surface of the reflection side is optionally uncoated or is provided with an anti-reflection coating, wherein the first and the second partial surfaces can supplement each other to form the entire surface of the reflection side.

The reflective layer can be applied to an outer surface of the reflection side of the second prism. The reflective coating can be a vapor-deposited layer consisting of silver (Ag) or aluminum (Al). The reflective coating ensures that light beams are reflected on an inner surface, i.e., in the prism body.

Light beams exit from the reflection side of the second prism through the non-reflectively coated part of the reflection side. These are the beams of light that enter the optical system at a wide angle from outside of the field of view and lead to the typical quadruple reflections in conventional optical systems. The occurrence of ghost images can be prevented or suppressed in the optical system according to elements of the optical system.

It is furthermore provided that a distance between the first entrance side and the reflection side in the first partial surface can always be larger than a distance between the first entrance side and the reflection side in the second partial surface. The non-reflectively coated second partial surface of the reflection side can therefore lie in a bottom, narrow, or respectively slim region of the second prism.

Furthermore, the optical system can be configured such that incident first light beams from the object space are reflected at the first partial surface of the reflective surface and are coupled into the left lens system channel, and incident second light beams from the object space are reflected at the second partial surface of the reflective surface and coupled into the right lens system channel.

For example, the optical axis of the entrance lens can define a position of a dividing line between the partial surfaces. This dividing line can also be for example 50%, 40%, 30% or 20% distant from the bottom edge, in each case with reference to the overall height of the surface in this direction.

Such object can be moreover achieved with a stereo video endoscope with a fixed, lateral viewing direction that can be configured such that it comprises an optical system according to one or more of the aforementioned embodiments.

The same or similar advantages can apply to the stereo video endoscope as were previously mentioned with respect to the optical system itself. With such a stereo video endoscope, ghost images also do not arise with beams of light that enter its optical systems at wide angles.

Such object can be furthermore achieved by a method for producing an optical system of a stereo video endoscope with a fixed, lateral viewing direction, wherein the stereo video endoscope comprises a laterally-viewing distal optical assembly and a proximal optical assembly, and wherein the proximal optical assembly comprises a left lens system channel and a right lens system channel that are designed similarly, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side, wherein the first and the second prisms can be selected or arranged such that the first entrance side and the reflection side enclose an angle that is greater than a total reflection angle of the second prism.

The selection can be carried out such that the optical system is configured such that incident light beams from a field of view of the optical system contact the reflection side of the second prism at an angle that is greater than the total reflection angle. In addition, the same or similar advantages also apply to the method as were already mentioned with regard to the optical system itself, and repetitions will therefore be avoided.

The method can also include providing the optical system with at least one aperture that borders the field of view of the optical system, wherein the angle between the first entrance side and the reflection side is set taking into account a material of the second prism that establishes a refraction index and hence a total reflection angle, and taking into account a maximum viewing angle that is established by the field of view such that total reflection of all incident light beams from the field of view occurs at the reflection side of the second prism.

Furthermore, the reflection side of the second prism can be optionally left uncoated, or can be provided with an anti-reflection coating.

Furthermore, the method can include providing a first partial surface of the reflection side of the second prism with a reflective coating, and a second partial surface of the reflection side can be optionally left uncoated or can be provided with an anti-reflection coating, wherein the first and the second partial surfaces can supplement each other to form the entire surface of the reflection side.

Such object can also be achieved by a method for repairing a stereo video endoscope with a lateral viewing direction, wherein an optical system of the stereo video endoscope comprises a laterally-viewing distal optical assembly and a proximal optical assembly, and wherein the proximal optical assembly comprises a left lens system channel and a right lens system channel that are designed similarly, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side, wherein this method is developed in that the deflection prism group is exchanged and replaced with a new deflection prism group, wherein the first and the second prism can be selected or arranged such that the first entrance side and the reflection side enclose an angle that is greater than a total reflection angle of the second prism.

By means of the method for repairing the stereo video endoscope, existing endoscopes can be created with regard to sensitivity to ghost images.

In the context of the present description, a coating of the reflection side is understood to be a reflective coating, for example, with silver (Ag) or aluminum (Al). If the reflection side is uncoated or partially coated, the reflection side accordingly does not have a reflective coating, or partially does not have a reflective coating.

Further features will become apparent from the description of the embodiments together with the claims and the attached drawings. Embodiments can fulfill individual features or a combination of several features.

BRIEF DESCRIPTION OF THE DRAWINGS

The embodiments are described below, without restricting the general idea of the invention, using exemplary embodiments with reference to the drawings, wherein express reference is made to the drawings with regard to all details that are not explained in greater detail in the text. In the following.

In the drawings, in each case the same or similar elements and/or parts are provided with the same reference numbers, so that in each case a repeated introduction is omitted.

DETAILED DESCRIPTION

Figure 1:
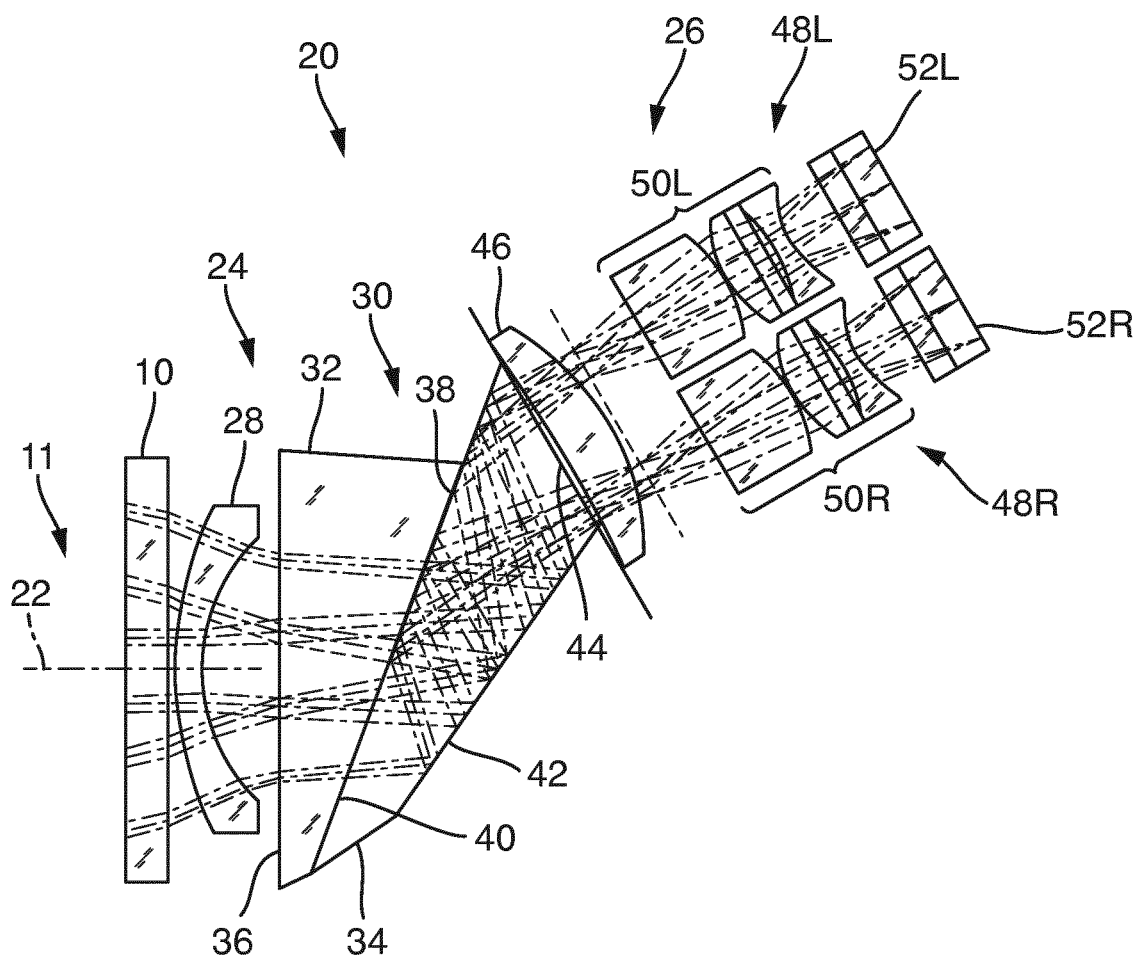
FIG. 1 illustrates a schematically simplified representation of an optical system of a stereo video endoscope according to the prior art in a side view.
Figure 2:
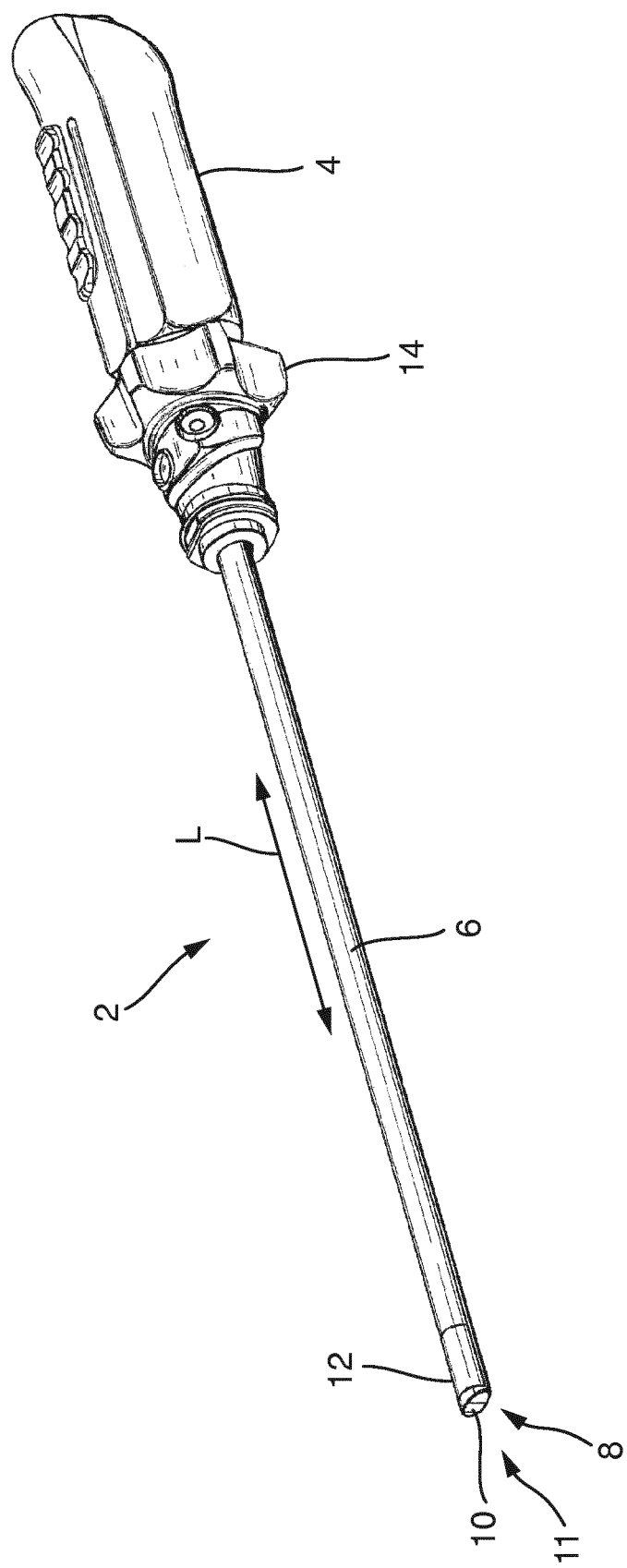
FIG. 2 illustrates a stereo video endoscope in a schematically simplified representation.

FIG. 2 shows a schematically simplified perspective representation of a stereo video endoscope 2 comprising a proximal handle 4 to which for example a rigid endoscope shaft 6 is connected. The endoscope shaft 6 can be both flexible or semi-flexible. An entrance window 10 through which light from an object space 11, for example from a surgical and/or observation field enters an optical system (not shown in FIG. 2) of the stereo video endoscope 2, is located on a distal tip 8 of the endoscope shaft 6. The optical system of the stereo video endoscope 2 is arranged for example in a distal section 12 of the endoscope shaft 6. The optical system images objects that are located in the object space 11 on image sensors. These image sensors are for example those with a high resolution such as HD, 4K or the following technologies.

The shown stereo video endoscope 2 is a surgical instrument. In addition, the endoscope has a fixed, lateral viewing direction. The entrance window 10 is mounted at an angle in the endoscope shaft 6 so that an optical axis of the entrance lens of the optical system (not shown) encloses a fixed angle with a direction of longitudinal extension L of the endoscope shaft 6 of the stereo video endoscope 2. This angle can be for example between 10° and 30°.

A change in the viewing direction about the longitudinal axis of the endoscope shaft 6 is effectuated by a rotation of the handle 4. The optical system in the distal section 12 also rotates during this rotation of the handle 4. To retain the horizontal position of the displayed image, the rotary wheel 14 is held while rotating the handle 4. As a result, the image sensors in the inside of the endoscope shaft 6 do not also perform the rotational movement.

Figure 3:
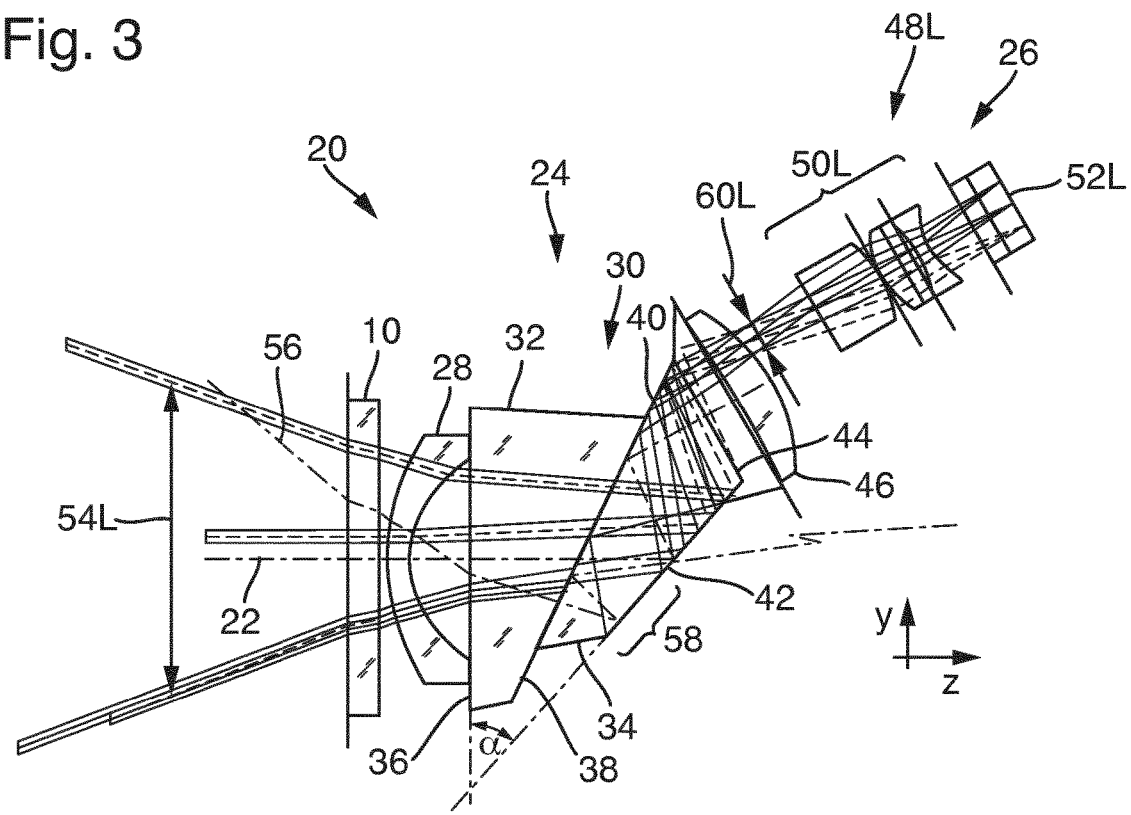
FIG. 3 illustrates a schematically simplified representation of the optical system of a stereo video endoscope, wherein the beam path of the left lens system channel is represented.

FIG. 3 shows an optical system 20 in a schematically simplified representation according to an exemplary embodiment. Only the left lens system channel 48L is portrayed in the optical system for reasons of simplifying the representation.

Figure 4:
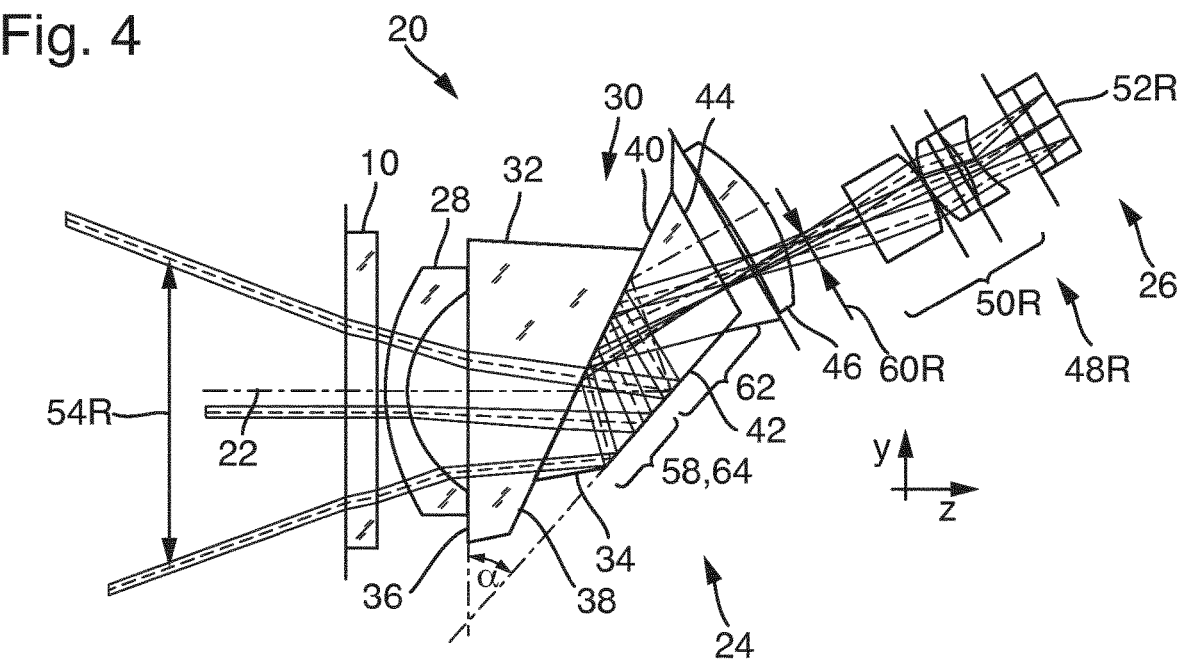
FIG. 4 illustrates a schematically simplified representation of the optical system of a stereo video endoscope, wherein the beam path of the right lens system channel is represented.

FIG. 4 shows a corresponding representation of an optical system 20 according to an exemplary embodiment, wherein the right lens system channel 48R is represented in this representation.

FIG. 3 shows the beam path of beams of light that enter the left lens system channel; correspondingly, FIG. 4 shows the beam path of beams of light that enter the right lens system channel 48R. The light beams that are imaged in the left lens system channel originate from a field of view of the left channel 54L; the light beams that are imaged in the right lens system channel 48R originate from a field of view of the right channel 54R.

FIG. 3 shows an example of a light beam 56 that enters the optical system 20 at a wide angle relative to the optical axis 22. It enters into a region of the second prism 34 that will also be termed the "B-down region". This B-down region 58 is typically not used by beams of light that are imaged in the left lens system channel 48L. The light beams that enter the right lens system channel (see FIG. 4) are contrastingly reflected in the B-down region 58 of the reflection side 42 of the second prism 34. It can accordingly happen that the light beam 56 which is reflected in the B-down region 58 of the second prism 34 enters the right lens system channel 48R and generates a ghost image there.

In order to inter alia suppress or completely eliminate this phenomenon, the optical system 20 is configured such that the first entrance side 36 of the first prism 32 and the reflection side 42 of the second prism 34 enclose an angle α that is greater than the total reflection angle $\theta_C$ of the second prism 34.

The total reflection angle $\theta_C$ is calculated using the known formula (1) as set forth above;

$$\Theta_C = \arcsin(n1/n2) \quad (1)$$

where n1=1 stands for air, and n2>1 is the refraction index of the material of the second prism 34.

The first and the second prism 32, 34 can be produced from the same or identical material. At least materials with at least approximately the same refraction index can be used for the two prisms 32, 34. For example, the two prisms 32, 34 can be made of the same glass.

The refraction index of the material is the refraction index that is used in Snell's law of refraction. It is therefore not the complex refraction index.

The optical system 20 is configured such that the light beams entering the optical system 20 from a field of view 54L, 54R contact the reflection side 42 of the second prism 34 at such an angle that is greater than the total reflection angle. It is therefore possible for the reflection side 42 of the second prism 34 to remain uncoated, i.e., not with a vapor-deposited reflective layer such as Al or Ag. It is also provided for the reflection side 42 of the second prism 34 to be provided with an anti-reflection coating as is for example known from photographic optical systems.

It is furthermore provided that the optical system 20 can comprise at least one aperture 60R, 60L that borders the field of view 54L, 54R of the optical system 20. In the portrayed exemplary example, separate apertures 60L, 60R are provided for the left and the right lens system channel 48L, 48R, namely the left aperture 60L and the right aperture 60R.

The angle α between the first entrance side 36 of the first prism 32 and the reflection side 42 of the second prism 34 is selected taking into account a material of the second prism 34 that establishes a refraction index n2 and hence a total reflection angle $\theta_C$, and taking into account a maximum viewing angle that is established by the field of view 54L, 54R such that total reflection occurs for all incident light beams from the field of view 54L, 54R by the reflection side 42 of the second prism 34.

Conversely, this means that light beams that enter the optical system 20 from outside of the field of view 54L, 54R, such as the light beam 56 that causes a ghost image in conventional systems, are not totally reflected on the reflection side 42 of the second prism 34. Such light beams leave the optical system 20, or more precisely the reflection side 42 of the second prism 34, and are absorbed for example by a black interior of a tube accommodating the optical system 20.

By optimizing the behavior between the angle of incidence controlled by the menisci or apertures 60R, 60L on the reflection side 42 of the second prism 34 for all beams that enter from within the fields of vision 54L, 54R, total reflection can be produced on the reflection side 42. For example, an angle of incidence at the first entrance side 36 of the first prism 32 must be −7.6° (the minus sign that is used means a clockwise rotation in the depiction in the figures), wherein the angle is α=36°, and S-LAH 58 is used as the material for the prisms. In such a case, all of the light beams contacting the reflection side 42 are totally reflected. A coating on this surface can be entirely dispensed with, or the surface can be provided with an anti-reflection coating.

According to another exemplary embodiment, a first partial surface 62 of the reflection side 42 of the second prism 34 can be provided with a reflective layer, and a second partial surface 64 of the reflection side 42 can be uncoated, or can be provided with an anti-reflection coating. The first and the second partial surface 62, 64 can be for example portrayed in FIG. 4. Furthermore, the second partial surface 64 can correspond to the B-down region 58, for example. The first and the second partial surface 62, 64 can supplement each other, for example, to form the entire surface on the reflection side 42. This makes it possible for light beams 56 that cause ghost images in conventional systems to leave the reflection side 42 of the second prism 34 in the B-down region 58.

The first and the second partial surface 62, 64 can be furthermore arranged on the reflection side 42 of the second prism 34 such that a spacing between the first entrance side 36 of the first prism 32 and the reflection side 42 of the second prism 34 is always greater in the first partial surface 62 than a corresponding spacing between the first entrance side 36 and the reflection side 42 in the second partial surface 64. In other words, the second partial surface 64 of the first entrance side 36 consistently lies closer than the first partial surface 62.

Different than shown in FIG. 4, the first and the second partial surfaces 62, 64 can overlap. In one exemplary embodiment, it can be provided for incident first light beams from an object space 11 to be reflected in the first partial surface 62 of the reflection surface 42 and to be coupled into the left lens system channel 48L. Incident second light beams from the object space 11 are reflected in the second partial surface 64 of the reflection surface 42 and coupled into the right lens system channel 48R.

In a method to produce an optical system 20 of a stereo video endoscope 2 with a fixed, lateral viewing direction that comprises a laterally-viewing distal optical assembly 24 and a proximal optical assembly 26, the first and the second prism 32, 34 of the deflection prism group 30 of the distal optical assembly 24 can be selected or arranged such that the first entrance side 36 of the first prism 32 and the reflection side 42 of the second prism 34 enclose an angle α that is greater than the total reflection angle $\theta_C$ of the second prism 34.

This selection and arrangement can comprise not only the geometric design of the first and second prism 32, 34 and their arrangement in the optical system 20, but can also the selection of the materials, or respectively glasses used to produce these prisms 32, 34 that determine the respective refraction index of the prisms 32, 34.

The procedure is similar in a method for repairing a stereo video endoscope 2 with a lateral viewing direction. For example, the deflection prism group 30 of a conventional optical system 20 is replaced with a deflection prism group 30 that fulfills the aforementioned requirements. It is also possible to completely exchange the entire distal optical assembly 24, or even the optical system 20.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Stereo video endoscope
4 Handle
6 Endoscope shaft
8 Distal tip
10 Entrance window
11 Object space
12 Distal section
14 Adjusting wheel
20 Optical system
22 Optical axis
24 Distal optical assembly
26 Proximal optical assembly
28 Entrance lens
30 Deflecting prism group
32 First prism
34 Second prism
36 First entrance side
38 First exit side
40 Second entrance side
42 Reflection side
44 Second exit side
46 Exit lens
48L Left lens system channel
48R Right lens system channel
50L Left lens group
50R Right lens group
52L Left image sensor
52L Right image sensor
54L Field of view of the left channel
54L Field of view of the right channel
56 Light beam
58 B-down region
60L Left aperture
60R Right aperture
62 First partial surface
64 Second partial surface
L Direction of longitudinal extension
α Angle
$\theta_C$ Total reflection angle

What is claimed is:

1. An optical system for use with a stereo video endoscope with a fixed, lateral viewing direction, the optical system comprising:
   a laterally-viewing distal optical assembly; and
   a proximal optical assembly comprising:
      a left lens system channel; and
      a right lens system channel similarly configured to the left lens system channel;
   wherein the distal optical assembly is configured to couple incident light from an object space into the left lens system channel and into the right lens system channel of the proximal optical assembly;
   the distal optical assembly sequentially comprises an entrance lens, a deflection prism group and an exit lens in a direction of the incident light;
   the deflection prism group sequentially comprises a first prism and a second prism in the direction of the incident light;
   the first prism comprises a first entrance side and a first exit side at an angle relative thereto;
   the second prism comprises a second entrance side, a reflection side and a second exit side; and
   the first entrance side of the first prism and the reflection side of the second prism enclose an angle that is greater than a total reflection angle of the second prism.

2. The optical system according to claim 1, wherein the distal optical assembly is configured such that the incident light from a field of view contact the reflection side of the second prism at an angle that is greater than the total reflection angle.

3. The optical system according to claim 2, further comprising at least one aperture that borders the field of view, wherein the angle between the first entrance side and the reflection side is selected based on a material of the second prism that establishes a refraction index and the total reflection angle, and a maximum viewing angle that is established by the field of view such that total reflection of all incident light beams from the field of view occurs at the reflection side of the second prism.

4. The optical system according to claim 3, further comprising one of an anti-reflection coating disposed on the reflection side of the second prism.

5. The optical system according to claim 1, further comprising one or more of a reflective coating disposed on a first partial surface of the reflection side of the second prism, and an anti-reflection coating on a second partial surface of the reflection side, wherein the first and the second partial surfaces supplement each other to form an entire surface of the reflection side.

6. The optical system according to claim 5, wherein a distance between the first entrance side and the reflection side in the first partial surface is larger than a distance between the first entrance side and the reflection side in the second partial surface.

7. The optical system according to claim 5, wherein incident first light beams from the object space are reflected at the first partial surface of the reflective surface and are coupled into the left lens system channel, and incident second light beams from the object space are reflected at the second partial surface of the reflective surface and coupled into the right lens system channel.

8. A stereo video endoscope with a fixed, lateral viewing direction, the stereo video endoscope comprising the optical system according to claim 1.

9. A method of forming an optical system of a stereo video endoscope with a fixed, lateral viewing direction, wherein the stereo video endoscope comprises a laterally-viewing distal optical assembly and a proximal optical assembly, and wherein the proximal optical assembly comprises a left lens system channel and a right lens system channel configured similarly to the left lens system channel, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side, wherein the method comprises:

selecting or arranging the first and the second prisms such that the first entrance side of the first prism and the reflection side of the second prism enclose an angle that is greater than a total reflection angle of the second prism.

10. The method according to claim 9, wherein the optical system is further provided with at least one aperture that borders the field of view of the optical system, the method further comprising selecting the angle between the first entrance side and the reflection side based on a material of the second prism that establishes a refraction index and the total reflection angle and a maximum viewing angle that is set by the field of view such that total reflection of all incident light beams from the field of view occurs at the reflection side of the second prism.

11. The method according to claim 10, further comprising providing an anti-reflection coating on the reflection side of the second prism.

12. The method according to claim 9, further comprising providing one or more of a reflective coating on a first partial surface of the reflection side of the second prism and an anti-reflection coating on a second partial surface of the reflection side, wherein the first and the second partial surfaces supplement each other to form the entire surface of the reflection side.

13. A method for repairing a stereo video endoscope with a lateral viewing direction, wherein an optical system of the stereo video endoscope comprises a laterally-viewing distal optical assembly and a proximal optical assembly, and wherein the proximal optical assembly comprises a left lens system channel and a right lens system channel configured similarly to the left lens system channel, and wherein the distal optical assembly is configured to couple incident light from an object space into the left lens system channel and into the right lens system channel of the proximal optical assembly, and wherein the distal optical assembly sequentially comprises an entrance lens, a deflection prism group and an exit lens in a direction of incident light, wherein the deflection prism group sequentially comprises a first prism and a second prism in the direction of incident light, wherein the first prism comprises a first entrance side and a first exit side at an angle relative thereto, and wherein the second prism comprises a second entrance side, a reflection side and a second exit side, wherein the method comprises:

replacing the deflection prism group with a replaced deflection prism group, wherein replaced defection prism group includes a replaced first prism and a replaced second prism selected or arranged such that the first entrance side of the replaced first prism and the reflection side of the replaced second prism enclose an angle that is greater than a total reflection angle of the second prism.

* * * * *